US010500033B2

(12) United States Patent
Naor et al.

(10) Patent No.: US 10,500,033 B2
(45) Date of Patent: Dec. 10, 2019

(54) EMBOLIC FILTER DEVICE AND METHOD OF USE THEREOF

(75) Inventors: Gil Naor, Hofit (IL); Yuval Shezifi, Haifa (IL)

(73) Assignee: Keystone Heart Ltd., Caesarea (IL)

( * ) Notice: Subject to any disclaimer, the term of this patent is extended or adjusted under 35 U.S.C. 154(b) by 1066 days.

(21) Appl. No.: 14/122,560

(22) PCT Filed: May 28, 2012

(86) PCT No.: PCT/IL2012/000208
§ 371 (c)(1),
(2), (4) Date: Jul. 21, 2014

(87) PCT Pub. No.: WO2012/160556
PCT Pub. Date: Nov. 29, 2012

(65) Prior Publication Data
US 2014/0336695 A1    Nov. 13, 2014

Related U.S. Application Data

(60) Provisional application No. 61/490,156, filed on May 26, 2011.

(51) Int. Cl.
*A61F 2/01* (2006.01)
(52) U.S. Cl.
CPC .......... *A61F 2/01* (2013.01); *A61F 2002/018* (2013.01); *A61F 2230/0006* (2013.01); *A61F 2230/0067* (2013.01); *A61F 2250/0067* (2013.01)
(58) Field of Classification Search
CPC ...... A61F 2/01; A61F 2/013; A61F 2002/016; A61F 2002/018
See application file for complete search history.

(56) References Cited

U.S. PATENT DOCUMENTS 6,652,556 B1   11/2003   VanTassel et al.
7,232,453 B2    6/2007   Shimon
(Continued)

FOREIGN PATENT DOCUMENTS

WO   WO-2006/131930 A2   12/2006
WO   WO-2010/026240 A1    3/2010

OTHER PUBLICATIONS

International Preliminary Report on Patentability for International Application No. PCT/IL2012/000208, dated Nov. 26, 2013 (8 pages).
(Continued)

*Primary Examiner* — Todd J Scherbel
(74) *Attorney, Agent, or Firm* — Inskeep IP Group, Inc.

(57) ABSTRACT

In general, the invention features an intra-vascular device for filtering or deflecting emboli or other large objects from entering a protected secondary vessel or vessels. The device of the invention may include a filter, an central member, additional supporting members, and a delivery cable and may serve to filter or deflect emboli or other large objects from entering protected secondary vessels. The device may be capable of collapse along its longitudinal axis for ease of delivery to the treatment site. The device may further be compatible with common delivery methods used in interventional cardiology (e.g., TAVI procedures). The device may be integrated into the delivery systems. In other embodiments the device may be detachable from the delivery system. Upon deployment, the device may be positioned so as to contact the orifice of one or more secondary blood vessels. Upon retrieval the device may be retracted in an orientation substantially similar to the original deployment orientation.

19 Claims, 7 Drawing Sheets

(56) References Cited

U.S. PATENT DOCUMENTS

| | | | |
|---|---|---|---|
| 8,062,324 B2 | 11/2011 | Shimon et al. | |
| 8,114,114 B2 * | 2/2012 | Belson | A61F 2/01 606/200 |
| 2002/0169437 A1 * | 11/2002 | Macoviak | A61B 17/12036 604/509 |
| 2006/0015138 A1 * | 1/2006 | Gertner | A61F 2/01 606/200 |
| 2008/0255603 A1 | 10/2008 | Naor et al. | |
| 2010/0179647 A1 * | 7/2010 | Carpenter | A61F 2/013 623/2.11 |
| 2011/0106137 A1 | 5/2011 | Shimon | |
| 2013/0184739 A1 * | 7/2013 | Brady | A61B 17/221 606/200 |

OTHER PUBLICATIONS

International Search Report for International Application No. PCT/IL2012/000208, dated Sep. 17, 2012 (4 pages).

Written Opinion of the International Searching Authority for International Application No. PCT/IL2012/000208, dated Sep. 17, 2012 (7 pages).

* cited by examiner

EMBOLIC FILTER DEVICE AND METHOD OF USE THEREOF

CROSS-REFERENCE TO RELATED APPLICATIONS

This application is the U.S. National Stage of PCT/IL2012/000208, filed May 28, 2012, which, in turn, claims benefit of U.S. Provisional Application No. 61/490,156, each of which is hereby incorporated by reference in its entirety.

FIELD OF THE INVENTION

The invention relates to devices for blocking emboli in an aorta from entering arteries.

BACKGROUND OF THE INVENTION

Devices such as vascular filters or other devices may be inserted into a blood vessel prior to or during a procedure or at another time. Such devices may be inserted by way of a catheter that may be threaded through a vein or artery and into, for example, an aorta or other vessel where the device may be released from the catheter and, for example, deployed. The device may filter, deflect, or block emboli or other objects from entering into a blood supply that feeds the brain.

SUMMARY OF THE INVENTION

In one aspect, the invention features an intra-vascular device for deflecting emboli including a substantially planar filter (e.g., a filter made from Nitinol mesh or perforated film) and a central member connected to the filter. The device can be configured such that, when deployed in a primary blood vessel, the central member partially obstructs one or more secondary blood vessels, and a portion of the central member extends from a horizontal plane of the filter into a secondary blood vessel. The device can be, when deployed in a primary blood vessel, capable of collapse along a longitudinal axis.

In the devices of the invention, the central member can be hollow. The central member can be capable of providing structural support and can further be capable of permitting the passage of a guidewire.

Any of the devices of the invention can include one or more additional members extending outwards from the central member. These additional members can be capable of providing structural support. These additional members can also be cylindrical and/or hollow. These additional members and/or the central member can include NiTi.

In any of the devices of the invention, the filter material can include braided, woven, or clustered material. In certain aspects, the filter can include laminated mesh. For example, the mesh can include polymeric film, e.g., perforated polymeric film.

The substantially planar filter can be adapted to conform to the vessel wall. In other aspects, the filter can include an outer skeleton. The outer skeleton can be capable of defining the edge of the substantially planar filter, or the filter material can extend beyond the outer skeleton, e.g., allowing the filter to conform to the vessel wall. In other aspects, the outer skeleton can be capable of controlling contact with the vessel wall.

In any of the devices of the invention, the filter can include Drawn Filled Tubing, e.g., including an outer layer of Nitinol and/or a core that includes tantalum and/or platinum.

In any of the devices of the invention, the device can further include a radiopacity marker (e.g., a bead or a clamp).

In yet other aspects, any device of the invention can include additional members that are located above and/or below the filter.

In any of the devices of the invention, the central member may also include a preformed bend. The preformed bend can be between 5° and 90°. In some aspects, the device also includes a second filter attached to the central member portion proximal to the first filter (and also, e.g., proximal to the preformed bend). The second filter can be sized to filter a secondary blood vessel. In other aspects, the central member can pass through the second filter. The second filter can have the capability of preventing particles from passing from the primary blood vessel to the secondary blood vessel.

In any of the devices of the invention, the substantially planar filter can further include a length to width ratio between 8:1 and 18:7. In other aspects, the central member can, e.g., pass through the filter and/or be connected to a delivery cable. In any of the devices of the invention, the device can have the capability of enclosure within an external sheath prior to deployment.

In another aspect, the invention features a method of preventing passage of a particle from the aorta into the left subclavian, left common carotid, or brachiocephalic artery including: inserting a guidewire through one of the left subclavian, left common carotid, or brachiocephalic artery and into the aortic arch; passing a catheter containing the device of any of the above devices in collapsed form over the guidewire and into the aortic arch; and retracting the catheter so that said device is deployed in the aortic arch, thereby preventing passage of a particle from the aorta into the left subclavian, left common carotid, or brachiocephalic artery.

In another aspect, the invention features a method of preventing passage of a particle from the aorta into the left subclavian, left common carotid, or brachiocephalic artery by inserting into the aorta any of the above-described devices such that the device prevents a particle from passing to the left subclavian, left common carotid, and brachiocephalic artery.

In any of the above methods, the device can be retrieved in an orientation substantially similar to the deployment orientation. Also, the secondary filter can prevent passage of particles into the brachiocephalic artery. The connection between the device and a delivery cable can be constant throughout insertion, deployment, and retrieval, and the devices can be enclosed within an external sheath prior to deployment.

As used herein, the term "central member" refers to a structural element within the perimeter of the filter that improves structural properties and facilitates insertion, deployment, and retrieval of the device.

As used herein, the term "substantially flat" refers to a radius of curvature of no more than 80 mm (e.g., 10 mm, 20 mm, 30 mm, 40 mm, 50 mm, 60 mm, or 70 mm).

As used herein, the term "blood" refers to all or any of the following: red cells (erythrocytes), white cells (leukocytes), platelets (thrombocytes), and plasma.

As used herein, the term "delivery cable" refers to any delivery system used in interventional cardiology to introduce foreign bodies to a treatment site (e.g., catheters, guidewires, tubes, and wires).

As used herein, the term "provide structural support" refers to the property contributing to shape and stiffness of the device.

As used herein, the term "wires" refers to any elongated structure (e.g., cords, fibers, yarns, filaments, cables, and threads) fabricated from any non-degradable material (e.g., polycarbonate, polytetrafluorothylene (PTFE), expanded polytetrafluorothylene (ePTFE), polyvinylidene fluoride, (PVDF), polypropylene, porous urethane, Nitinol, fluropolymers (Teflon®), cobalt chromium alloys (CoCr), and para-aramid (Kevlar®), or textile (e.g., nylon, polyester (Dacron®), or silk).

DETAILED DESCRIPTION OF THE PREFERRED EMBODIMENTS

The invention features an intravascular device for preventing particles from passing from a primary blood vessel (e.g., the aorta) to one or more secondary blood vessels (e.g., the left subclavian, left common carotid, and brachiocephalic artery). In general, the devices of the invention feature a filter with an internal structure, including, e.g., a central member. This internal structure provides, e.g., structure to the filter and can, e.g., facilitate the control of the filter within the anatomy of the primary blood vessel. For example, this internal structure (e.g., central member) can permit an operator to control the orientation of the device within the primary blood vessel and press the device against certain features of the primary blood vessel (e.g., to press the device against the orifice of one or more secondary blood vessels or against the walls of the primary blood vessel). The devices of the invention can also feature an outer skeleton (e.g., FIG. 4, item 100) connected to the internal structure. The outer skeleton can provide additional structural support for the device and can facilitate the creation of a seal between the filter of the device and a blood vessel wall. Alternatively, the filter itself may create a seal against the blood vessel wall by extending beyond the perimeter of the outer skeleton.

The device of the invention may include a filter, a central member, additional supporting members, and a delivery cable. The device can filter and/or deflect emboli or other large objects from entering protected secondary vessels. The device may be capable of collapse along its longitudinal axis for ease of delivery to the treatment site. The device may further be compatible with common delivery methods used in interventional cardiology (e.g., TAVI procedures). The device may be integrated into a delivery system. In other embodiments the device may be detachable from the delivery system. Upon deployment, the device may be positioned so as to contact the orifice of one or more secondary blood vessels in, e.g., the aortic arch. Upon retrieval the device may be retracted in orientation substantially similar to the original deployment orientation.

Figure 1:
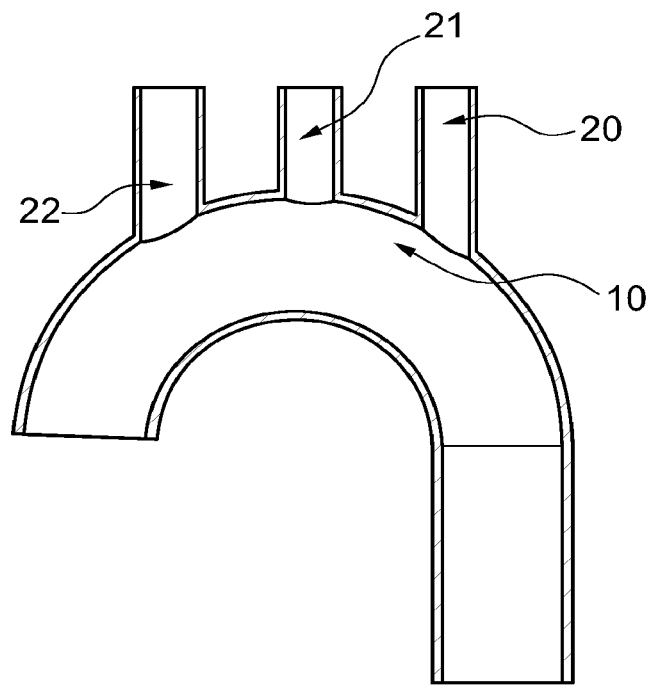
FIG. 1 is a schematic diagram of the guidewire (10) passed through the left subclavian artery (20) and into the aortic arch.
Figure 2:
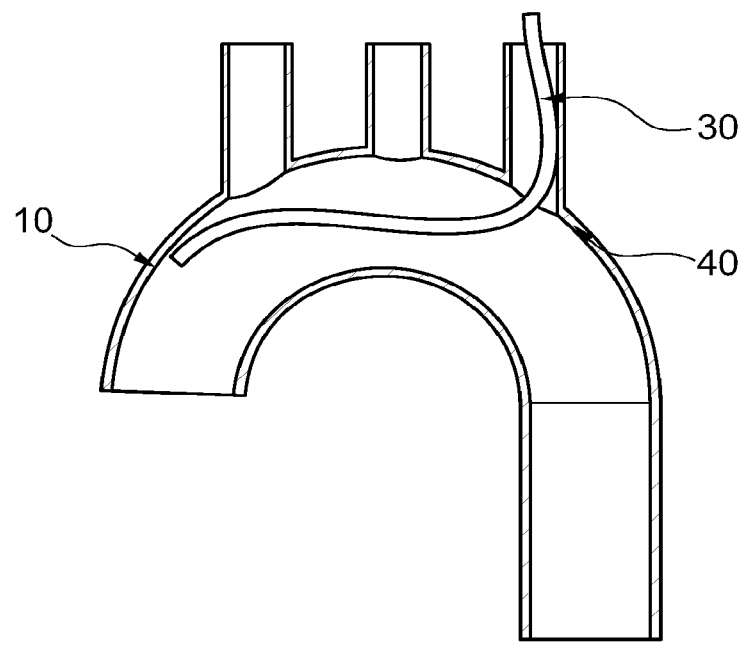
FIG. 2 is a schematic diagram of an external sheath system (30) advanced over the guidewire (10) until marker band (40) positioned on the sheath indicates the correct position, as determined by the manufacturer.

Reference is made to FIG. 1 and FIG. 2: FIG. 1 is a schematic diagram of a guide wire (10) passing through the left subclavian artery (20) into the aortic vessel in the direction of the ascending aorta, and FIG. 2 is a schematic diagram of an external sheath system (30) is advanced over the guidewire (10) until marker band (40) positioned on the sheath indicates the correct position, as determined by the manufacturer. In some embodiments, the device (11) may be contracted when the device is folded in an external sheath (30), and the filter area may expand when the filter is unfolded and deployed. Forward movement of outer tube will collapse the device, while retrograde movement will allow deployment. The length of the device may be from approximately 80 mm to 90 mm (e.g., 80 mm, 82 mm, 84 mm, 86 mm, 88 mm, or 90 mm), or otherwise as may be necessary to approximate a distance between an upper wall of an ascending aorta, upstream of an opening of a brachiocephalic artery, and at an upper wall of a descending aorta downstream of an opening of a left subclavian artery. In some embodiments, the length of the device may be reduced to the length necessary to approximate a distance between the upper wall of a descending aorta or an ascending aorta and the opening of the targeted artery (e.g., the left subclavian, left common carotid, or brachiocephalic artery). The width of the device may be from 10 mm to 35 mm (e.g., 10 mm, 15 mm, 20 mm, 25 mm, 30 mm, or 35 mm), or otherwise as may approximate an internal diameter of an aorta or the diameter of a secondary blood vessel. The device may be inserted into the aorta or introduced into a blood vessel in a collapsed form and may assume an extended form upon its release from a sheath or other insertion or positioning mechanism.

Figure 3:
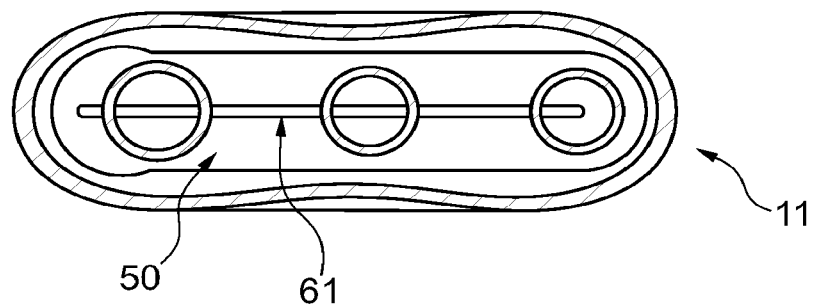
FIG. 3 is a schematic diagram of device (11) deployed to protect the left subclavian, left common carotid, and brachiocephalic artery.
Figure 4:
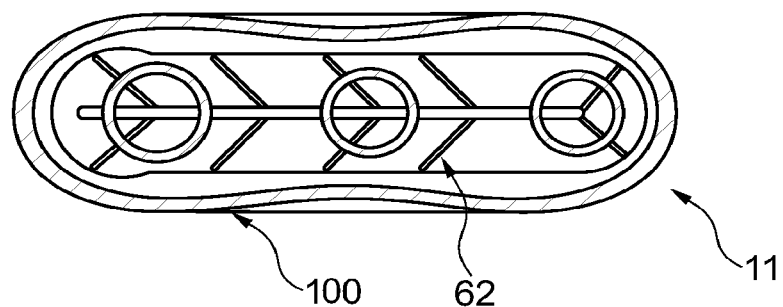
FIG. 4 is a schematic diagram of device (11) deployed to protect the left subclavian, left common carotid, and brachiocephalic artery. The depicted device includes radiating supporting members (62).

Reference is made to FIG. 3 and FIG. 4: FIG. 3 is a schematic diagram of an underside view of device (11) deployed in the aortic arch to protect all carotid branches (e.g., left subclavian (20), left common carotid (21), and brachiocephalic artery (22)), and FIG. 4 is a schematic diagram of the deployed device (11) with additional members (62) extending from the central member (61). In some embodiments, it is desirable to incorporate radiopaque elements into the intra-vascular device. Such radiopaque elements can be affixed to, or incorporated into the intra-vascular device (e.g., affixed to the central member (61), filter (50), optional second filter (70, FIG. 6), or radiating supporting members (62)). The radiopaque element can be a bead or clamp (e.g., as depicted in FIG. 7C). In the case of a clamp, the element can be crimped onto the intra-vascular device. In any of the embodiments of the invention, radiopaque material can be incorporated into wire forming the central member (61), filters (50 or 70), or radiating supporting members (62) of the intra-vascular device (see, e.g., FIG. 7B). For example, portions of the central member or filter mesh can be constructed out of DFT wire. Such wire can contain, e.g., a core of tantalum and/or platinum and an outer material of, e.g., Nitinol (see, e.g., FIG. 7A).

Figure 7A:
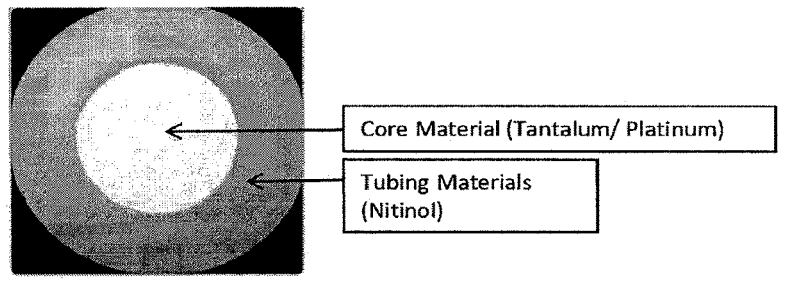
FIG. 7A is a photograph of a cross section of DFT wire.
Figure 7B:
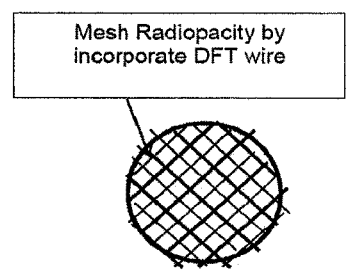
FIG. 7B is a schematic diagram of a filter mesh containing DFT wire.
Figure 8A:
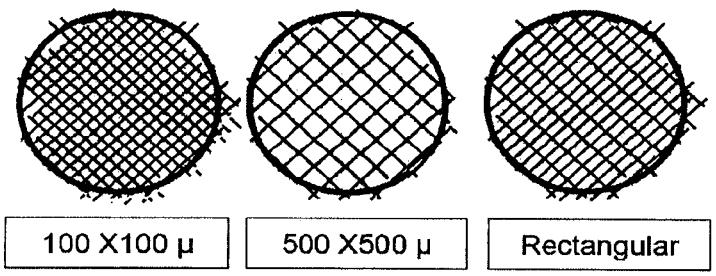
FIG. 8A is a schematic diagram showing filter meshes of the indicated pore sizes.
Figure 8B:
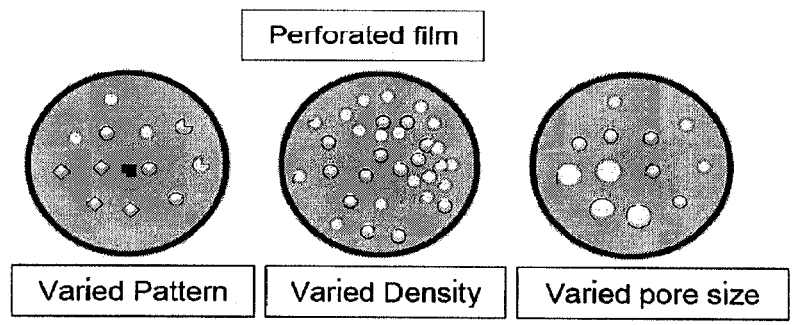
FIG. 8B is a schematic diagram showing perforated films with the indicated patterns, sizes, and densities of pores.
Figure 8C:
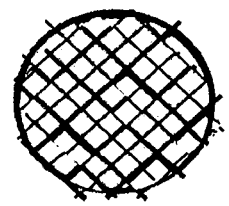
FIG. 8C is a schematic diagram showing a filter mesh with a combination of DFT (Drawn Filled Tubing) and Nitinol wires.

In some embodiments, filters (50 or 70) may be or include a fine wire netting or mesh (e.g., as depicted in FIGS. 8A and 8C), or perforated film (e.g., as depicted in FIG. 8B), such as a mesh or sheet having holes or porosity of 50-950 microns (e.g., 50, 150, 250, 350, 450, 550, 650, 750, 850, 950, or more microns). The perforated film may be perforated prior to the inclusion with the device. The film may also be perforated post inclusion with the device (e.g., by laser drilling or electric sparks). In embodiments where a perforated film is present, the pores can have constant or varied pore patterns, constant or varied pore densities, and/or constant or varied pore sizes (FIG. 8B). The filters (50 or 70) may be braided, weaved, clustered, knitted, or knotted. The filters (50 or 70) may be a non-degradable material (e.g., polycarbonate, polytetrafluoroethylene (PTFE), expanded polytetrafluorothylene (ePTFE), polyvinylidene fluoride, (PVDF), polypropylene, porous urethane, Nitinol, fluropolymers (Teflon®), cobalt chromium alloys (CoCr), and para-aramid (Kevlar®)), or textile (e.g., nylon, polyester (Dacron®), or silk). The filter may be a combination of materials (e.g., the combination of DFT and Nitinol wires as depicted in FIGS. 7A and 7B). The filters (50 or 70) may also be coated with an anti-thrombogenic agent to prevent a thrombogenic reaction.

In some embodiments, one or more members (61 or 62) or filters (50 or 70) may include a lumen, such as, for example, a hollow wire, which may hold, for example, a medicament that may be released into an artery or area where the device is implanted. The central member can have, e.g., a length of 100%, 95%, 90%, 85%, 80%, 75%, 70%, 60%, 50%, 40%, 30%, 20%, 10%, or less of the length of the longest region of the intra-vascular device. The radiating supporting members can have, e.g., a length of 100%, 95%, 90%, 85%, 80%, 75%, 70%, 60%, 50%, 40%, 30%, 20%, 10%, or less of the width of the widest region of the intra-vascular device.

In some embodiments, device (11) may assume a substantially elliptical or elongated shape. Other shapes may be used. Because the aortic anatomy can vary between individuals, embodiments of the intra-vascular device of the invention are shaped to adapt to a variety of aortic anatomies. The size of the device (11) may be pre-sized and pre-formed to accommodate various patient groups (e.g., children and adults) or particular aortic anatomy. The delivery cable (60) may be made from a non-degradable material (e.g., NiTi). The delivery cable (60) may also be pre-shaped to press against the top aortic wall lightly, thus allowing the device to remain along the vessel wall and clear of the passage of trans-femoral accessories that may be used in therapeutic cardiovascular procedures (e.g., TAVI procedures). This pre-shape may include a bend (71) (e.g., 5°, 10°, 15°, 20°, 25°, 30°, 35°, 40°, 45°, 50°, 55°, 60°, 65°, 70°, 75°, 80°, 85°, or 90°) to further facilitate device deployment flush to the a vessel wall. The device may vary in length from 10 mm to 120 mm (e.g., 25 mm, 45 mm, 60 mm, 75 mm, 90 mm, or 105 mm) and width from 5 mm to 70 mm (e.g., 10 mm, 20 mm, 30 mm, 40 mm, 50 mm, or 60 mm).

In certain embodiments, the stiffness of the intra-vascular device will be determined by the stiffness of the filter, central member, or radiating supporting members. For example, the device can be stiffened by the inclusion of heavier gauge wire or by the inclusion of stiffer central member or radiating supporting members. Furthermore, multiple wires of a certain gauge can be wound together to increase the stiffness of the device (e.g., the device can include 2, 3, 4, 5, or more wires of to increase the stiffness of the intra-vascular device).

Figure 5A:
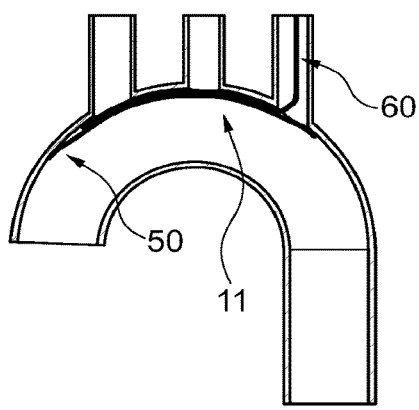
FIG. 5A is a schematic diagram of device (11) wherein filter (50) is pre-attached to a delivery cable (60) (e.g., a NiTi tube), and the filter (50) is positioned below the central member.
Figure 5B:
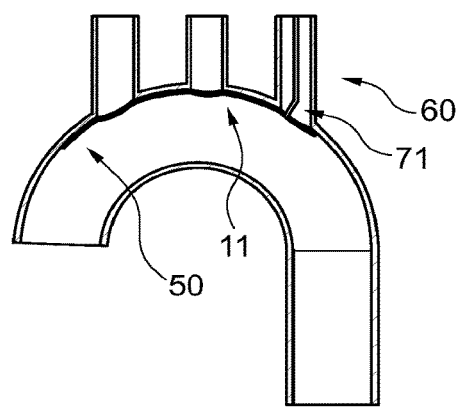
FIG. 5B is a schematic diagram of device (11) wherein a preformed bend (71) is present, filter (50) is pre-attached to a delivery cable (60) (e.g., a NiTi tube), and the filter is positioned above the central member.

Reference is made to FIGS. 5A and 5B: FIG. 5A is a schematic diagram of device (11) with filter (50) positioned below the central member (61) and FIG. 5B is a schematic diagram of device (11) with filter (50) positioned above central member (61). In some embodiments, device (11) may include both a central member (61) and radiating supporting members (62) extending from central member. The filter (50) may also be positioned either above or below these radiating supporting members. In some embodiments, delivery cable (60) is integrated with filter (50) via a connection between delivery cable (60) and central member (61). The connection between delivery cable (60) and central member (61) may be either permanent (e.g., crimped, glued, soldered, or bonded) or semi-permanent (e.g., clipped, latched, hooked, clamped, or screwed) to allow the detachment of filter (50) from delivery cable (61) after deployment.

Figure 6:
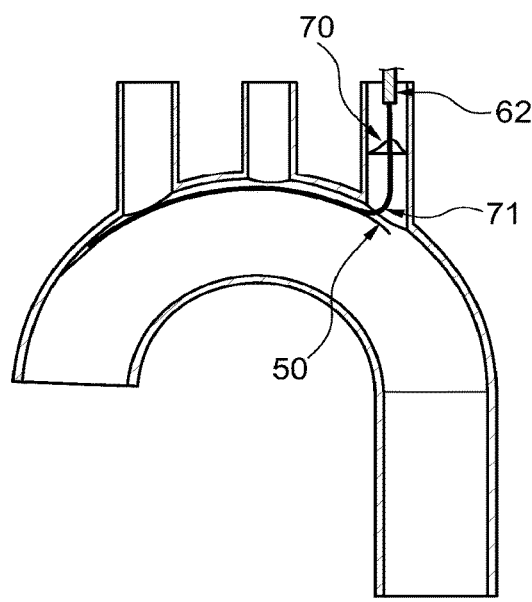
FIG. 6 is a schematic diagram of device in an alternate configuration wherein the filter (50) is deployed to cover the right subclavian and brachiocephalic artery while secondary filter (70) covers the left subclavian artery. Transition point (71) marks a post-deployment and pre-formed bend in delivery cable (e.g., 5°, 10°, 15°, 20°, 25°, 30°, 35°, 40°, 45°, 50°, 55°, 60°, 65°, 70°, 75°, 80°, 85°, or 90°). The device is depicted post deployment with external sheath (62) retracted.
Figure 7C:
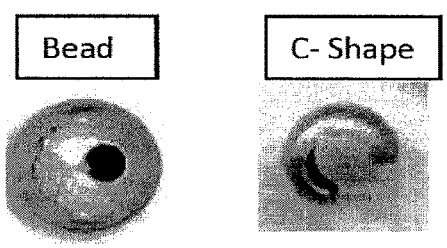
FIG. 7C is a photograph of a radiopacity bead and clamp element for use in the invention.

Reference is made to FIG. 6, which is a schematic diagram of filter (50) positioned so that the opening of the brachiocephalic and left common carotid artery are covered by the filter. In some embodiments, the left subclavian artery is covered by a secondary filter (70). Secondary filter (70) may be attached to delivery cable (60). Secondary filter (70) may be conical in shape with the delivery cable (60) passing through the apex of the filter. The secondary filter (70) may also be substantially flat with delivery cable (60) passing through any point within secondary filter (70) so long as delivery cable (60) is connected to filter (70), e.g., at all points along the delivery cable's outer perimeter. The width of the widest portion of secondary filter (70) may be pre-sized and pre-formed to accommodate particular subclavian arterial anatomy (e.g, 2, 4, 6, or 8 mm in width). Other shapes may be used.

Figure 9A:
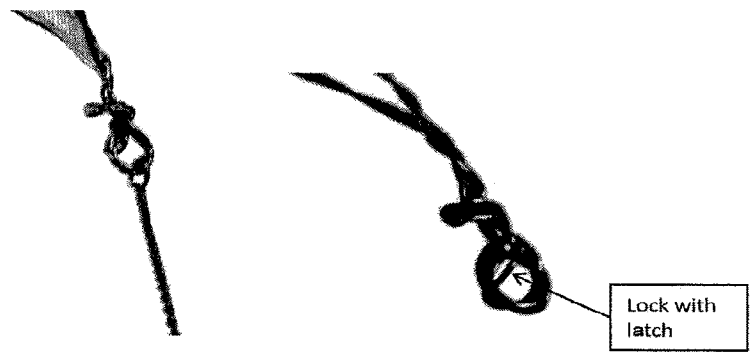
FIGS. 9A-9C are photographs showing a variety of mechanisms for connecting the device to a catheter or delivery cable.
Figure 9B:
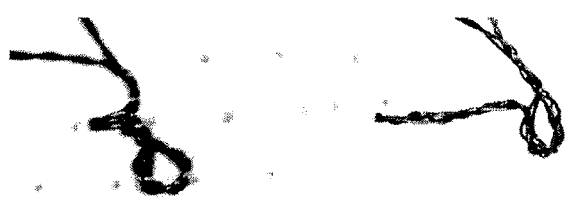
Figure 9B:
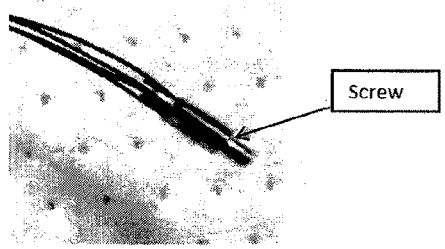
Figure 9C:

Reference is made to FIGS. 9A-9C. As described above, a variety of configurations can be used to connect the intra-vascular filter to a plunger (e.g., a plunger connected with a delivery cable disposed within a catheter). FIG. 9A depicts a locking mechanism with a latch. FIG. 9B depicts a screw whereby the intra-vascular device can be mated with a screw on a plunger. FIG. 9C depicts a release and recapture hook for connecting the intra-vascular device with a plunger. In some embodiments, a hook may include a latch or wire strand that may be part of the device.

In other embodiments, the filter (50), catheter, member (61), or delivery cable (60) may end in a loop and may be threaded through a latch. When so threaded, a wire or catheter fitted with a looped end may be clicked into a hook and may securely push the device into place or pull the device out of position from a blood vessel (e.g., the aorta).

In some embodiments, the hook may end in a ball-tip so that strands from the filter (50) do not fray or scratch the vessel wall or the inner tube of a catheter.

In other embodiments, a clasp at an end of the device may be pressed into or onto a clasp at, for example, an end of a catheter or delivery cable (60), and the two clasps may be joined by such pressing. In some embodiments, the device may be rotated clockwise or counter-clockwise respectively.

In an installed position, the intra-vascular device may be inserted into a first blood vessel. In some embodiments, the first blood vessel may be or include an aorta, though the device may be inserted into other vessels. The filter (50) of the device may be positioned so that an opening of a second blood vessel is covered by the filter, so that, for example, large particles are filtered, blocked, or deflected from entering, for example, the left subclavian, left common carotid, or brachiocephalic artery, or any combination thereof (e.g., the left subclavian, left common carotid, and brachiocephalic artery; the left subclavian and left common carotid artery; left common carotid and brachiocephalic artery; and the left common carotid and brachiocephalic artery). The space under filter (50) may allow unfiltered blood to pass by the branch artery of the aorta. The space in the aorta that is left below the filter means that not all blood passing through the aorta is subject to the filtering or deflecting process of filter (30). In an installed position, the device remains substantially flat (e.g., does not exceed a radius of curvature of 80 mm).

Figure 10:
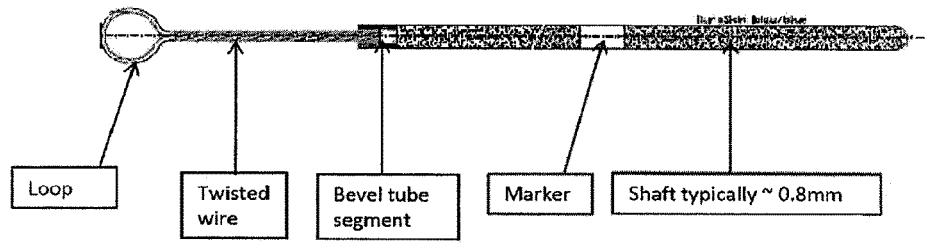
FIG. 10 is a schematic diagram of a side view of a plunger for use in introducing devices of the invention into a subject, e.g., through a catheter.

Reference is made to FIG. 10. A shaft or plunger for use in connection with the device can terminate in a loop (as depicted in FIG. 10) or a screw. In embodiments where a loop is present, the loop can be generated by winding two wires together leaving a loop at the distal end (FIG. 10). The shaft or plunger can, e.g., include a radiopaque element. Furthermore, the shaft or plunger can feature a rectilinear (e.g., square) or curved (e.g., oval or circular) cross section. Differences in cross sectional shape can have advantageous properties with respect to controlling the positioning of the intra-vascular device within the aorta. In certain embodiments, a shaft or plunger may replace or be used in conjunction with delivery cable (61).

In still other embodiments, device (11) may be adapted for use with other embolism protection devices (e.g., those described U.S. application Ser. Nos. 13/300,936, and 13/205,255; in U.S. Publication Nos. 2008-0255603 and 2011-0106137; and in U.S. Pat. Nos. 8,062,324 and 7,232,453), each of which is hereby incorporated by reference in its entirety.

All publications and patents cited in this specification are incorporated herein by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An intra-vascular device comprising;
a filter for preventing embolic particles from passing therethrough with a blood flow downstream of an aortic valve into side branch vessels of said aortic arch to the brain of a patient while allowing passage of blood flow from an aortic arch to at least one of said side branch vessels, and said filter comprising an outer skeleton around and connected to said filter, said outer skeleton providing structural support and configured to create a seal between said device and a wall of said aortic valve;
a central member connected to said filter, wherein, when said device is deployed in a primary blood vessel having more than one side branch vessels, said filter having a length for covering at least two of said more than one side branch vessels;
wherein said device is capable of collapse along a longitudinal axis;
wherein said central member is a wire member running longitudinally along a center of said device, and disposed entirely within a periphery of said outer skeleton of said filter when said filter is fully deployed, said central member providing structural support with respect to shape and stiffness of the device; and
said device is permanently connected to a delivery cable.

2. The device as in claim 1, wherein said central member is hollow.

3. The device as in claim 2, wherein said hollow central member permits the passage of a guidewire.

4. The device as in claim 1, wherein said device further comprises one or more additional members extending outwards from the central member.

5. The device as in claim 4, wherein said one or more additional members provide structural support.

6. The device as in claim 4, wherein said one or more additional members comprise NiTi.

7. The device as in claim 1, wherein said filter comprises braided, woven, or clustered material.

8. The device as in claim 1, wherein said filter comprises Nitinol mesh.

9. The device as in claim 1, wherein said filter comprises perforated film.

10. The device as in claim 8, wherein said mesh is laminated.

11. The device as in claim 1, wherein said filter is adapted to conform to the vessel wall.

12. The device as in claim 1, wherein said outer skeleton defines the edge of the filter.

13. The device as in claim 1, wherein the filter extends beyond the outer skeleton, allowing the filter to conform to the wall of said primary blood vessel.

14. The device as in claim 1, wherein said device further comprises a radiopacity marker.

15. The device as in claim 14, wherein said radiopacity marker is a bead or a clamp.

16. The device as in claim 4, wherein said one or more additional members are located above the filter.

17. The device as in claim 4, wherein said one or more additional members are located below the filter.

18. The device as in claim 1, wherein said central member further comprises a preformed bend proximal to said filter.

19. The device as in claim 1, wherein said filter has a length to width ratio between 8:1 and 18:7.

\* \* \* \* \*